(12) United States Patent
Shelchuk

(10) Patent No.: US 7,792,585 B1
(45) Date of Patent: Sep. 7, 2010

(54) EXPEDITED SET-UP OF MULTI-ELECTRODE LEAD (MEL)

(75) Inventor: Anne M. Shelchuk, Cupertino, CA (US)

(73) Assignee: PaceSetter, Inc., Sunnyvale, CA (US)

( * ) Notice: Subject to any disclaimer, the term of this patent is extended or adjusted under 35 U.S.C. 154(b) by 782 days.

(21) Appl. No.: 11/750,153

(22) Filed: May 17, 2007

(51) Int. Cl.
*A61N 1/365* (2006.01)

(52) U.S. Cl. .................................. 607/27; 607/115

(58) Field of Classification Search ............. 607/6, 607/8, 9, 27, 28, 115–123
See application file for complete search history.

(56) References Cited

U.S. PATENT DOCUMENTS

| | | | |
|---|---|---|---|
| 4,922,607 A | 5/1990 | Doan | |
| 4,995,389 A | 2/1991 | Harris | |
| 5,246,014 A | 9/1993 | Williams et al. | |
| 5,350,410 A | 9/1994 | Kleks et al. | |
| 5,584,873 A | 12/1996 | Shoberg et al. | |
| 5,643,330 A * | 7/1997 | Holsheimer et al. | 607/46 |
| 5,948,014 A | 9/1999 | Valikai | |
| 6,466,810 B1 | 10/2002 | Ward et al. | |
| 6,546,288 B1 | 4/2003 | Levine | |
| 6,640,136 B1 | 10/2003 | Helland et al. | |
| 6,882,887 B1 | 4/2005 | Shelchuk | |
| 6,978,178 B2 | 12/2005 | Sommer et al. | |
| 7,027,852 B2 | 4/2006 | Helland | |
| 7,123,969 B1 | 10/2006 | Chitre | |
| 7,647,108 B2 * | 1/2010 | Freeberg | 607/28 |
| 2003/0083724 A1 * | 5/2003 | Jog et al. | 607/122 |
| 2006/0058588 A1 | 3/2006 | Zdeblick | |

* cited by examiner

*Primary Examiner*—Carl H Layno
*Assistant Examiner*—Brian T Gedeon
(74) *Attorney, Agent, or Firm*—Steven M. Mitchell

(57) ABSTRACT

Methods and systems are provided for expediting set-up of a multi-electrode lead (MEL). In accordance with specific embodiments, such an MEL includes N groups of electrodes, with each of the N groups including at least M electrodes, where N≧2 and M is ≧2. Electrodes in a same group are within 5 mm of one another. Electrodes in separate groups are at least 10 mm from one another. Specific embodiments relate to methods for identifying cathode-anode electrode configurations that can be used to not exceed a maximum acceptable capture threshold, and that provide a sensed intrinsic R-wave amplitude of at least a minimum acceptable sensing threshold. Such thresholds can be default values, or can be defined by a user (e.g., clinician, physician, nurse, or the like).

22 Claims, 11 Drawing Sheets

☐ Cathode
☐ Anode

Option 1:
Capture Threshold: 0.8V @ 0.5ms
Sense threshold: 12.1 mV
Impedance: 890 ohms
Pace Energy: 0.41 uJ

Option 2:
Capture Threshold: 0.9V @ 0.5ms
Sense threshold: 9.9 mV
Impedance: 900 ohms
Pace Energy: 0.45 uJ

EXPEDITED SET-UP OF MULTI-ELECTRODE LEAD (MEL)

FIELD OF THE INVENTION

Embodiments of the present invention relate to implantable cardiac systems and leads for use therewith. More specifically, embodiments of the present invention relate to systems and methods for expediting set-up of a multi-electrode implantable cardiac lead.

BACKGROUND

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous extracardiac stimulation, e.g., of surrounding skeletal muscle tissue, the patient's phrenic nerve or the patient's diaphragm.

The "capture threshold" is defined as the lowest stimulation pulse energy at which capture occurs. By stimulating the heart chambers at or just above this threshold, comfortable and effective cardiac stimulation can be provided without unnecessary depletion of battery energy. The capture threshold, however, is extremely variable from patient-to-patient due to variations in electrode systems used, electrode positioning, physiological and anatomical variations of the heart itself, and so on. Furthermore, a capture threshold may vary over time within a patient as, for example, fibrotic encapsulation of an electrode can occur after implantation of the electrode.

Implantable lead(s), attached to an implantable cardiac device (ICD), such as a pacemaker, is/are used to deliver such stimulation pulses to the myocardium. Some such leads are multi-electrode leads (MELs), meaning they include multiple electrodes for use in pacing and/or sensing. Multi-electrode leads allow for more flexibility in pacing and sensing, as compared to single electrode leads. Generally, the more electrodes on a lead, the more flexibility provided. However, a challenge when using leads with greater numbers of electrodes is increased complexity when setting up the electrode configuration. For example, one left-sided lead design includes four electrode arrays (also referred to as groups or bands) with four electrodes each, thus resulting in a single lead with sixteen electrodes. An example of an electrode that can include sixteen (and even more) electrodes is disclosed in U.S. Patent Publication No. 2006/0058588 (U.S. patent application Ser. No. 11/219,305), entitled "Methods and Apparatus for Tissue Activation and Monitoring" (Zdeblick), published Mar. 16, 2006 (filed Sep. 1, 2005), which is incorporated herein by reference. With such a complex multi-electrode lead there can be hundreds and possibly thousands of different cathode-anode combinations (also referred to as cathode-anode electrode configurations).

Presuming it takes on the order of about 90 seconds to test each possible cathode-anode electrode configuration, it would take hours upon hours for a clinician to test all possible electrode configurations for multi-electrode leads having numerous electrodes. This would be true even if the clinician used an auto set-up programmer, if the programmer were to try to test all possible combinations. Accordingly, it would be beneficial if more efficient methods and systems were developed from assisting with the configuration of such multi-electrode leads.

SUMMARY

Embodiments of the present invention relate to methods and systems for expediting set-up of a multi-electrode lead (MEL). In accordance with specific embodiments, such an MEL includes N groups of electrodes, with each of the N groups including at least M electrodes, where $N \geq 2$ and M is $\geq 2$. Electrodes in a same group are within 5 mm of one another. Electrodes in separate groups are at least 10 mm from one another.

Specific embodiments relate to methods for identifying cathode-anode electrode configurations that can be used to not exceed a maximum acceptable capture threshold, and that provide a sensed intrinsic R-wave amplitude of at least a minimum acceptable sensing threshold. Such thresholds can be default values, or can be defined by a user (e.g., clinician, physician, nurse, or the like).

Each electrode that can be used as a cathode can be identified by connecting each electrode of the MEL individually as the cathode, and determining, for each electrode individually connected as the cathode, a capture threshold and a sensed intrinsic R-wave amplitude. In accordance with specific embodiments, when an electrode is individually connected as the cathode (for the purpose of testing the electrode's candidacy as the cathode), all the electrodes in another group of electrodes are electrically connected together as the anode. The another group, can be an adjacent group of electrodes. Where an electrode has two adjacent groups of electrodes, the more proximal group of electrodes can be connected together as the anode, in specific embodiments. In other embodiments, when an electrode is individually connected as the cathode (for the purpose of testing the electrode's candidacy as a cathode), all the other electrodes in the same group of electrodes are electrically connected together as the anode. In still other embodiments, when an electrode is individually connected as the cathode (for the purpose of testing the electrode's candidacy as a cathode), one or more electrode on a different lead is connected as the anode, or an electrically conductive housing of the implantable cardiac stimulation device is connected as the anode.

In accordance with specific embodiments, data indicative of the capture threshold and the sensed intrinsic R-wave amplitude, for each electrode individually connecting as the cathode is stored. Based on the stored data, each electrode that achieves both a capture threshold that does not exceed a maximum acceptable capture threshold, and a sensed intrinsic R-wave amplitude that at least reaches a minimum acceptable sensing threshold, is identified as an electrode that can be used as the cathode.

In accordance with specific embodiments, a graphical representation of the MEL is provided to a user in a manner that shows the user each electrode that is a candidate for use as the cathode. Thereafter, if desired, a user can adjust at least one of the maximum acceptable capture threshold, and the minimum acceptable sensing threshold. After this occurs, the electrode(s) that is/are cathode candidates are updated substantially instantaneously in view of the updated thresholds, by using the stored data (i.e., because the various other steps do not have to be repeated).

After the candidate cathode(s) is/are identified, candidate anode(s) is/are identified. In accordance with specific embodiments, for each electrode of the MEL identified as an electrode that can be used as the cathode, there is the identification of one or more other electrode in the same group that can be used as a corresponding anode. A benefit of having the cathode and anode be electrodes in a same group is that such a configuration avoids extracardiac stimulation. In specific embodiments, the identification of candidate anode(s) can be accomplished by connecting, individually as the anode, each other electrode in the same group as the electrode that can be used as the cathode, while the electrode that can be used as the cathode is connected as the cathode; and determining, for each cathode-anode combination, a capture threshold and a sensed intrinsic R-wave amplitude. Data indicative of the capture threshold and the sensed intrinsic R-wave amplitude is stored, for each tested cathode-anode electrode configuration. Based on the stored data, each other electrode connected as the anode that provided a cathode-anode electrode configuration that achieves both a capture threshold that does not exceed the maximum acceptable capture threshold, and a sensed intrinsic R-wave amplitude that at least reaches the minimum acceptable sensing threshold, is identified as an electrode that can be used as the anode.

In accordance with specific embodiments, graphical representations of all the identified cathode-anode electrode configurations are provided to a user, and the user can select which configuration to use. In other embodiments, only the best available cathode-anode electrode configuration is graphically provided to the user. For example, the best candidate cathode-anode electrode configuration can be the configuration that achieves the lowest capture threshold that does not exceed the maximum acceptable capture threshold, and a achieves sensed intrinsic R-wave amplitude that at least reaches the minimum acceptable sensing threshold.

This summary is not intended to be a complete description of, or limit the scope of, the invention. Alternative and additional features, aspects, and objects of the invention can be obtained from a review of the specification, the figures, and the claims.

DETAILED DESCRIPTION

Figure 1:
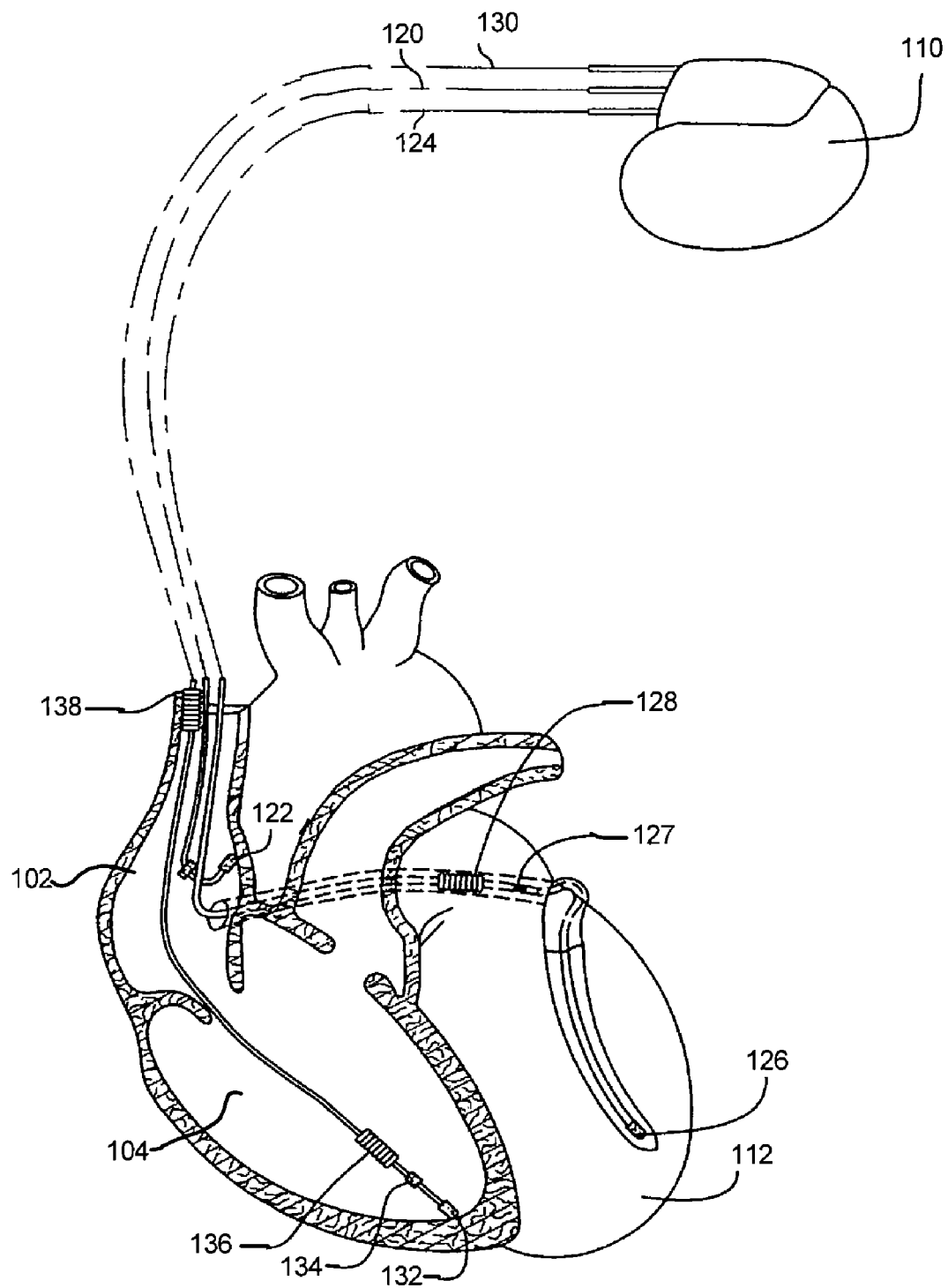
FIG. 1 is a simplified, partly cutaway view illustrating an exemplary implantable cardiac stimulation device in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Exemplary Implantable Cardiac Stimulation Device

FIG. 1 illustrates an exemplary cardiac stimulation device 110 in electrical communication with a patient's heart 112 by way of three leads 120, 124 and 130 suitable for sensing cardiac electrogram signals and also delivering multi-chamber stimulation and shock therapy. To sense atrial cardiac signals and to provide right atrial chamber stimulation therapy, the cardiac stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the cardiac stimulation device 110 is coupled to a "coronary sinus" lead 124 designed for placement in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 124 is designed to receive atrial and ventricular cardiac signals and to deliver left ventricular pacing therapy using at least a left ventricular tip electrode 26, left atrial pacing therapy using at least a left atrial ring electrode 127, and shocking therapy using at least a left atrial coil electrode 128.

The cardiac stimulation device 110 is also shown in electrical communication with the patient's heart 12 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals, and delivering stimulation in the form of pacing and shock therapy to the right ventricle.

Figure 2:
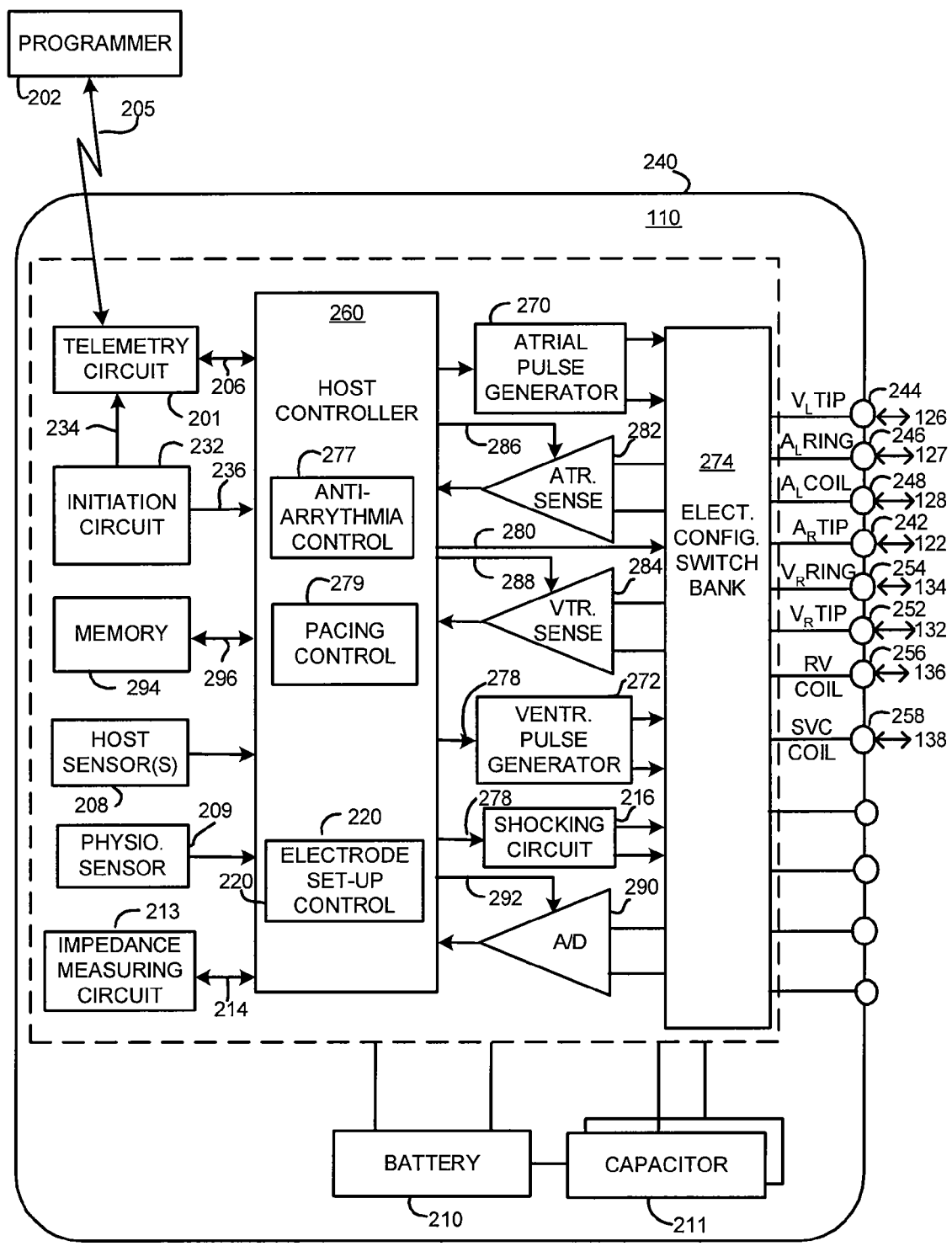
FIG. 2 is a functional block diagram of the exemplary multi-chamber implantable cardiac stimulation device of FIG. 1, illustrating the basic elements that provide cardioversion, defibrillation and/or pacing stimulation in four chambers of the heart.

FIG. 2 illustrates a simplified block diagram of the multi-chamber implantable cardiac stimulation device 110 which is capable of sensing cardiac electrogram signals, and also treating both fast and slow arrhythmias with stimulation therapy, including cardioversion, defibrillation, pacing stimulation. While a particular multi-chamber cardiac stimulation device is shown, this is for illustration purposes only and one of skill in the art could readily duplicate, eliminate or disable the appropriate circuitry in any desired combination to provide a device capable of sensing cardiac electrogram signals, treating the appropriate chamber(s) with cardioversion, defibrillation and/or pacing stimulation without departing from the scope of the invention.

Referring to FIG. 2, cardiac stimulation device 110 includes a housing 240 which is often referred to as a "can", "case" or "case electrode", and which may be programmably selected to act as the return electrode for all "unipolar" modes. Housing 240 may be used as a return electrode alone or in combination with one or more of the coil electrodes 128, 136, or 138, for shocking purposes. Housing 240 further includes a connector (not shown) having a plurality of terminals, 242, 244, 246, 248, 252, 254, 256, and 258 (shown schematically and, for convenience, the names of the exemplary electrodes to which they are connected are shown next to the terminals).

To achieve right atrial sensing and pacing, the connector includes at least a right atrial tip terminal 242 adapted for connection to the right atrial (AR) tip electrode 122. To achieve left chamber sensing, pacing and/or shocking, the connector includes at least a left ventricular (VL) tip terminal 244, a left atrial (AL) ring terminal 246, and a left atrial (AL) shocking terminal (coil) 248, which are adapted for connection to the left ventricular tip electrode 126, the left atrial ring electrode 127, and the left atrial coil electrode 128, respectively. To support right chamber sensing, pacing and/or shocking, the connector further includes a right ventricular (VR) tip terminal 252, a right ventricular (VR) ring terminal 254, a right ventricular (RV) shocking terminal (coil) 256, and an SVC shocking terminal (coil) 258, which are adapted for connection to the right ventricular tip electrode 132, right ventricular ring electrode 134, the RV coil electrode 136, and the SVC coil electrode 138, respectively.

At the core of cardiac stimulation device 110 is a programmable microcontroller, host controller 260, which controls the various modes of stimulation therapy. As is well known in the art, host controller 260 can include a microprocessor, or equivalent control circuitry or processor, designed for controlling the delivery of stimulation therapy, and may further include RAM or ROM memory, logic and timing circuitry, state machine circuitry, and I/O circuitry. Typically, host controller 260 includes the ability to process or monitor input signals (data) as controlled by program code stored in a designated block of memory. The details of the design and operation of host controller 260 are not critical to the present invention. Rather, any suitable host controller 260 may be used that carries out the functions described herein. The use of microprocessor-based control circuits for performing timing and data analysis functions is well known in the art.

As shown in FIG. 2, an atrial pulse generator 270 and a ventricular pulse generator 272 generate pacing stimulation pulses for delivery by the right atrial lead 120, the right ventricular lead 130, and/or the coronary sinus lead 124 via a switch bank 274. It is understood that in order to provide stimulation therapy in each of the four chambers of the heart, the atrial pulse generator 270 and the ventricular pulse generator 272 may include dedicated, independent pulse generators, multiplexed pulse generators, or shared pulse generators. The atrial pulse generator 270 and the ventricular pulse generator 272 are controlled by host controller 260 via appropriate control signals 276 and 278, respectively, to trigger or inhibit the stimulation pulses.

Host controller 260 further includes pacing control unit 279 which is used to control the timing of such stimulation pulses (e.g., pacing rate, atrio-ventricular (A-V) delay, atrial interconduction (A-A) delay, ventricular interconduction (V-V) delay, pacing mode, etc.), as well as to keep track of the timing of refractory periods, PVARP intervals, noise detection windows, evoked response windows, alert intervals, marker channel timing, etc.

The switch bank 274 includes a plurality of electrically configurable switches for connecting the desired electrodes to the appropriate I/O circuits, thereby providing complete electrode programmability. Accordingly, the switch bank 274, in response to a control signal 280 from host controller 260, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch bank 274 is configured to allow the paralleling (or averaging) of the multiple RV electrodes to simulate a large electrode for accurate sensing of the T-wave.

Atrial sensing circuits 282 and ventricular sensing circuits 284 may also be selectively coupled to the right atrial lead 120, coronary sinus lead 124, and the right ventricular lead 130, through the switch bank 274, for detecting the presence of cardiac activity in each of the four chambers of the heart. Accordingly, the atrial and ventricular sensing circuits 282 and 284 may include dedicated sense amplifiers, multiplexed amplifiers, or shared amplifiers. The switch bank 274 determines the "sensing polarity" of the cardiac signal by selectively closing the appropriate switches. In this way, the clinician may program the sensing polarity independent of the stimulation polarity. Each of the sensing circuits, 282 and 284 preferably employ one or more low power, precision amplifiers with programmable gain and/or automatic gain control, bandpass filtering, and a threshold detection circuit, to selectively sense the cardiac signal of interest. The automatic gain control enables the cardiac stimulation device 110 to deal effectively with the difficult problem of sensing the low amplitude signal characteristics of atrial or ventricular fibrillation.

The outputs of the atrial and ventricular sensing circuits 282 and 284 are connected to host controller 260 for triggering or inhibiting the atrial and ventricular pulse generators 270 and 272, respectively, in a demand fashion, in response to the absence or presence of cardiac activity, respectively, in the appropriate chambers of the heart. The atrial and ventricular sensing circuits 282 and 284, in turn, receive control signals over signal lines 286 and 288 from host controller 260, for controlling the gain, threshold, polarization charge removal circuitry (not shown), and the timing of any blocking circuitry (not shown) coupled to the inputs of the atrial and ventricular sensing circuits 282 and 284.

Cardiac signals are also applied to the inputs of an analog-to-digital (A/D) data acquisition system 290. Data acquisition system 290 is configured to acquire intracardiac electrogram signals, convert the raw analog data into digital signals, and store the digital signals for later processing and/or telemetric transmission to an external device 202. Data acquisition system 290 is coupled to the right atrial lead 120, the coronary sinus lead 124, and the right ventricular lead 130 through switch bank 274 to sample cardiac signals across any pair of desired electrodes. Data acquired by data acquisition system 290 (and optionally stored) can be used for subsequent analysis to guide the programming of the device, appropriately adjust pacing interval parameters, select optimum pacing intervals, and/or select appropriate anti-arrhythmia therapy.

Advantageously, data acquisition system 290 may be coupled to host controller 260 or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. Host controller 260 detects a depolarization signal during a window following a stimulation pulse, the presence of which indicates that capture has occurred. Host controller 260 enables capture detection by triggering the ventricular pulse generator 272 to generate a stimulation pulse, starting a capture detection window using the timing circuitry within host controller 260, and enabling data acquisition system 290 via control signal 292 to sample the cardiac signal that falls in the capture detection window and, based on the amplitude of the sampled cardiac signal, determines if capture has occurred.

One function of the cardiac stimulation device 110 can be to operate as an implantable cardioverter/defibrillator ("ICD") device. That is, cardiac stimulation device 110 detects the occurrence of an arrhythmia, and automatically applies an appropriate electrical shock therapy to the heart aimed at terminating the detected arrhythmia. To this end, anti-arrhythmia control unit 277 of control host controller 260 further controls a shocking circuit 216 by way of a control signal 218. The shocking circuit 216 generates shocking pulses of low (up to 0.5 joules), moderate (0.5-10 joules), or high (11-40 joules) energy, as controlled by host controller 260. Such shocking pulses are applied to the patient's heart through at least two shocking electrodes, as shown in this embodiment, selected from the left atrial coil electrode 128, the RV coil electrode 136, and/or the SVC coil electrode 138 (FIG. 1). As noted above, the housing 140 may act as an active electrode in combination with the RV electrode 136, or as part of a split electrical vector using the SVC coil electrode 138 or the left atrial coil electrode 128 (e.g., using the RV electrode as a common electrode). The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

For arrhythmia detection, the anti-arrhythmia control unit 277 of host controller 260 utilizes the atrial and ventricular sensing circuits 282 and 284 to sense cardiac signals, for determining whether a rhythm is physiologic or pathologic. The timing intervals between sensed events (e.g., P-waves, R-waves, and depolarization signals associated with fibrillation which are sometimes referred to as "F-waves" or "Fib-waves") are then classified by anti-arrhythmia control unit 277 of host controller 260 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Host controller 260 is further coupled to a memory 294 by a suitable data/address bus 296, where the programmable operating parameters used by host controller 260 are stored and modified, as required, in order to customize the operation of the cardiac stimulation device 110 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 112 within each respective tier of therapy. A feature of the cardiac stimulation device 110 is the ability to sense and store a relatively large amount of data (e.g., from data acquisition system 290), which data may then be used for subsequent analysis and also guiding the programming of the cardiac stimulation device 110. The host controller 260 can also be connected to host sensor(s) 208, a physiologic sensor 209, and an impedance measuring circuit 213, as shown.

Advantageously, the operating parameters of the cardiac stimulation device 110 may be non-invasively programmed into the memory 294 through a telemetry circuit 201 in telemetric communication with an external programmer 202, such as a, transtelephonic transceiver, or a diagnostic system analyzer. Additionally, telemetry circuit 201 may be used to guide the device 110 through electrode set-up algorithms of the present invention, which are discussed in more detail below.

A handshake signal can be sent from the programmer 202 (or other external device) to the telemetry circuit 201 so that the external device can be identified to the telemetry circuit 201 thereby defining what operations may be performed by the device. The programmer 202 can program the cardiac stimulation device 110 under the control of a physician as described in more detail with respect to FIG. 3. For examples of such programmers, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No.

6,275,734 entitled "Efficient Generation of Sensing Signals in an Implantable Medical Device such as a Pacemaker or ICD" (note: this relates to transfer of EGM data) (McClure et al.), which patents are hereby incorporated herein by reference.

Cardiac stimulation device 110 further includes initiation circuit 232. Initiation circuit 232 may comprise magnet detection circuitry. Initiation circuit 232 is coupled to host controller 260 by connection 236 and/or to telemetry circuit 201 by connection 234. The purpose of the initiation circuit is to detect an initiation signal from outside the patient. For example, a magnet placed over the cardiac stimulation device 110 may be used as the initiation signal, which signal may be used by a clinician to initiate various test functions of the cardiac stimulation device 110 and/or to signal host controller 260 that an external programmer 202 is in place to receive or transmit data to host controller 260 through the telemetry circuit 201. Initiation circuit 232 may also be used to activate electrode set-up algorithms of the present invention.

An electrode set-up control 220 of host controller 260 can process EGM signals to monitor for capture during pacing and to measure R-waves during sensing. The electrode set-up control 220 can cause the performance of steps of FIGS. 6-8, possibly under the control of an external device (e.g., an external programmer 202). Additionally, the electrode set-up control 220 can also configure electrodes in specific configurations, as instructed by an external device, such as the external programmer 202. This can be accomplished, e.g., by sending signals to the switch bank 274, as well as to switching circuitry of multi-electrode leads where appropriate. The electrode set-up control 220, and/or a separate component, can also be used to detect capture thresholds, which are discussed in more detail below. While shown as being part of the host controller 220, portions of, of the entire electrode set-up control 220 can be external to the controller 260, and can include software, firmware, hardware or combinations thereof.

Cardiac stimulation device 110 additionally includes a power source such as a battery 210 that provides operating power to all the circuits shown in FIG. 2. For a cardiac stimulation device 110, which employs shocking therapy, the battery 210 must be capable of operating at low current drains for long periods of time and also be capable of providing high-current pulses (for charging capacitor 211) when the patient requires a shock pulse. Battery 210 must preferably have a predictable discharge characteristic so that elective replacement time can be detected. Accordingly, cardiac stimulation device 110 can employ lithium/silver vanadium oxide batteries.

Exemplary Programmer

Figure 3:
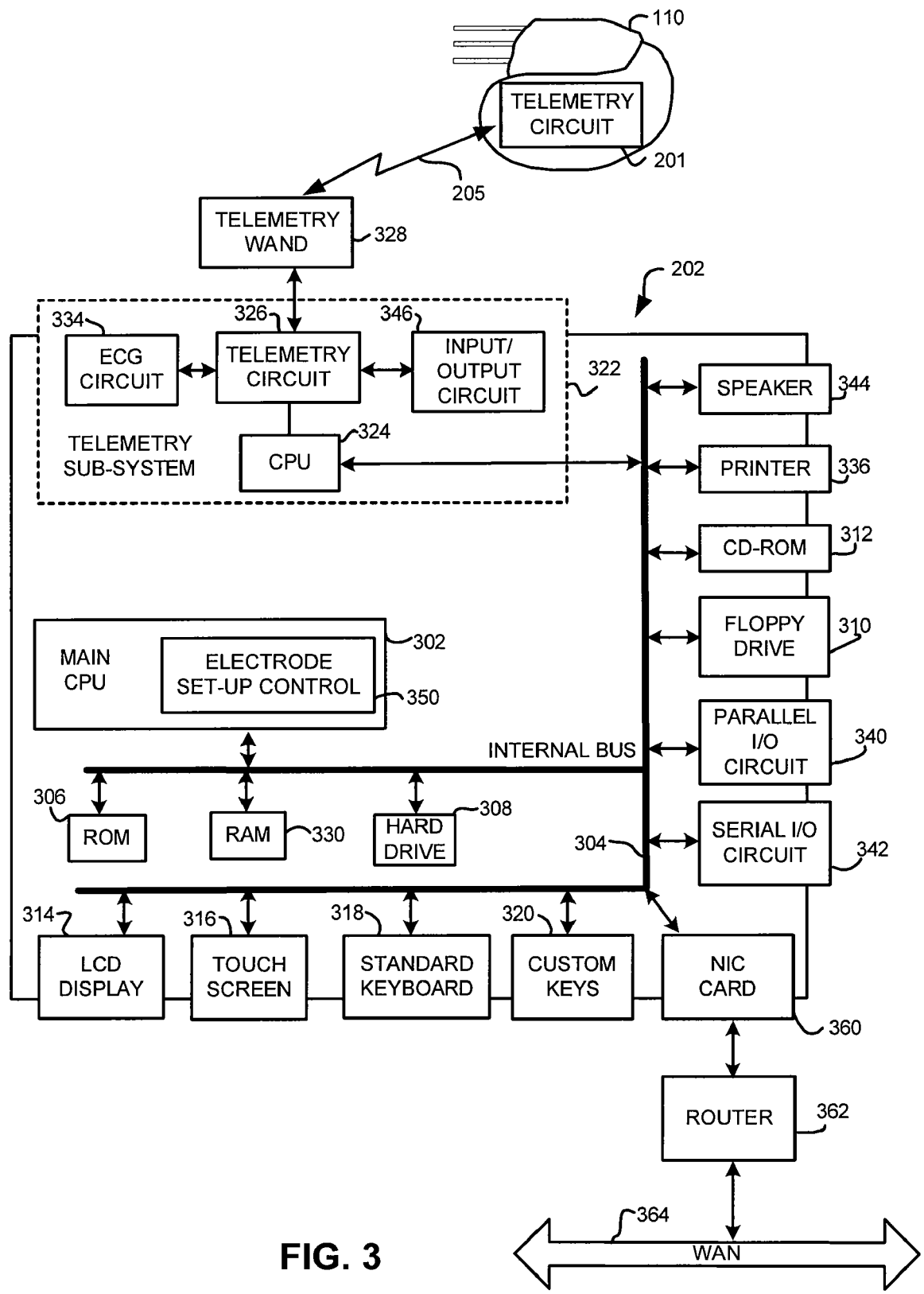
FIG. 3 is a functional block diagram illustrating components of an exemplary programmer for use in programming the implantable cardiac stimulation device of FIGS. 1 and 2.

FIG. 3 illustrates components of an exemplary programmer 202 for use in programming an implantable cardiac stimulation device, including setting up electrode configurations of an implantable cardiac stimulation device. Briefly, the programmer 202 permits a physician or other authorized user to program the operation of the implantable cardiac stimulation device 110 and to retrieve and display information received from the implantable cardiac stimulation device 110 such as EGM data and device diagnostic data. Additionally, the programmer 202 may receive and display ECG data from separate external ECG leads that may be attached to the patient. Further, the programmer 220 is capable causing the implantable cardiac stimulation device to perform functions necessary to complete certain electrode set-up algorithms of the present invention. Depending upon the specific programming of the programmer, programmer 202 may also be capable of processing and analyzing data received from the implantable cardiac stimulation device 110 and from ECG leads 332 to, for example, render preliminary diagnosis as to medical conditions of the patient or to the operations of the implantable cardiac stimulation device 110.

Now, considering the components of the programmer 202 by reference to FIG. 3, operations of the programmer 202 can be controlled by a CPU 302, which may be a generally programmable microprocessor or microcontroller or may be a dedicated processing device such as an application specific integrated circuit (ASIC) or the like. Software instructions to be performed by the CPU can be accessed via an internal bus 304 from a read only memory (ROM) 306 and random access memory 330. Additional software may be accessed from a hard drive 308, floppy drive 310, and CD ROM drive 312, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 314 or other suitable computer display device. To this end, the CPU may, for example, display a menu of specific programming parameters of the implantable cardiac stimulation device 110 to be programmed or may display a menu of types of diagnostic data to be retrieved and displayed. In response thereto, the physician enters various commands via either a touch screen 316 overlaid on LCD display 314 or through a standard keyboard 318 supplemented by additional custom keys 320, such as an emergency VVI (EVVI) key. The EVVI key sets the implantable cardiac stimulation device 110 to a safe VVI mode with high pacing outputs. This ensures life sustaining pacing operation in nearly all situations but by no means is it desirable to leave cardiac stimulation device 110 in the EVVI mode at all times.

Typically, the physician initially controls the programmer 202 to retrieve data stored within the implanted medical device and to also retrieve ECG data from ECG leads (examples discussed above with reference to FIGS. 1 and 2) coupled to the patient's myocardium. To this end, CPU 302 transmits appropriate signals to a telemetry circuit 322, which provides components for directly interfacing with implantable cardiac stimulation device 110. The telemetry subsystem 322 can includes its own separate CPU 324 for coordinating the operations of the telemetry subsystem 322. The main CPU 302 of the programmer 202 communicates with telemetry subsystem CPU 324 via internal bus 304. The telemetry subsystem 322 additionally includes a telemetry circuit 326 connected to a telemetry wand 328, which cooperate to receive and transmit signals electromagnetically from telemetry circuit 201 of the implantable cardiac stimulation device 110. The telemetry wand 328 is placed over the chest of the patient near the implanted cardiac stimulation device 110 to permit reliable transmission of data, over telemetric link 205, between the telemetry wand and the implantable cardiac stimulation device 110. Typically, at the beginning of the programming session, the external programming device controls the implantable cardiac stimulation device 110 via appropriate signals generated by telemetry wand 328 to output all previously recorded patient and device diagnostic information. Patient diagnostic information includes, for example, measured physiological variables data, recorded EGM data and statistical patient data such as the percentage of paced versus sensed heartbeats. Device diagnostic data includes, for example, information representative of the operation of the implantable cardiac stimulation device 110 such as lead impedances, battery voltages, battery recommended replacement time (RRT) information and the like. Data retrieved from the implantable cardiac stimulation device 110 is stored by the external programmer 202 either within a random access memory (RAM) 330, a hard drive 308, within a floppy diskette placed within a floppy drive 310, etc. Additionally, or in the alternative, data may be permanently or semi-permanently stored within a compact disk (CD) or other digital media disk, if the overall system is configured with a drive for recording data onto digital media disks, such as a write once read many (WORM) drive.

Patient and device diagnostic data stored within the implantable cardiac stimulation device 110 can be transferred to the programmer 202. Further, the implantable cardiac stimulation device 110 can be instructed to perform an electrode set-up algorithm of the present invention, details of which are provided below.

The programmer 202 can also include a network interface card ("NIC") 360 to permit transmission of data to and from other computer systems via a router 362 and wide area network ("WAN") 364. Alternatively, the programmer 202 might include a modem for communication via the public switched telephone network (PSTN). Depending upon the implementation, the modem may be connected directly to internal bus 304 may be connected to the internal bus via either a parallel port 340 or a serial port 342. Data transmitted from other computer systems may include, for example, data regarding medication prescribed, administered or sold to the patient.

The CPU 302 can include an electrode set-up control 350 that can control the performance of the steps described below with reference to FIGS. 6-8, and/or instruct the implantable stimulation device 110 to perform such steps. The electrode set-up control 350 of CPU 302 can operate in concert with the electrode set-up control 220 of device 110, or independent thereof. The programmer 202 receives data from the implantable cardiac stimulation device 110, including parameters representative of the current programming state of the implantable cardiac stimulation device 110. Under the control of the physician, programmer 202 displays the current programming parameters and permits the physician to reprogram the parameters. To this end, the physician enters appropriate commands via any of the aforementioned input devices and, under control of the CPU 302, the programming commands are converted to specific programming parameters for transmission to the implantable cardiac stimulation device 110 via the telemetry wand 328 to thereby reprogram the implantable cardiac stimulation device 110. Prior to reprogramming specific parameters, the physician may control the external programmer to display any or all of the data retrieved from the implantable cardiac stimulation device 110, including displays of ECGs, displays of electrodes that are candidates as cathodes and/or anodes, and statistical patient information. Any or all of the information displayed by programmer 202 may also be printed using a printer 336.

A speaker 344 is included for providing audible tones to the user, such as a warning beep in the event improper input is provided by the physician. Telemetry subsystem 322 may additionally include an input/output circuit 346 which can control the transmission of analog output signals, such as ECG signals output to an ECG machine or chart recorder. Other peripheral devices may be connected to the external programmer 202 via parallel port 340 or a serial port 342 as well. Although one of each is shown, a plurality of input output (IO) ports might be provided.

With the programmer 202 configured as shown, a physician or other authorized user can retrieve, process and display a wide range of information received from the implantable cardiac stimulation device 110 and reprogram the implantable cardiac stimulation device 110, including configurations of leads, if needed. The descriptions provided herein with respect to FIG. 3 are intended merely to provide an overview of the operation of the exemplary programmer 202 and are not intended to describe in detail every feature of the hardware and software of the device and are not intended to provide an exhaustive list of the functions performed by the device.

Exemplary Multi-Electrode Leads

Figure 4A:
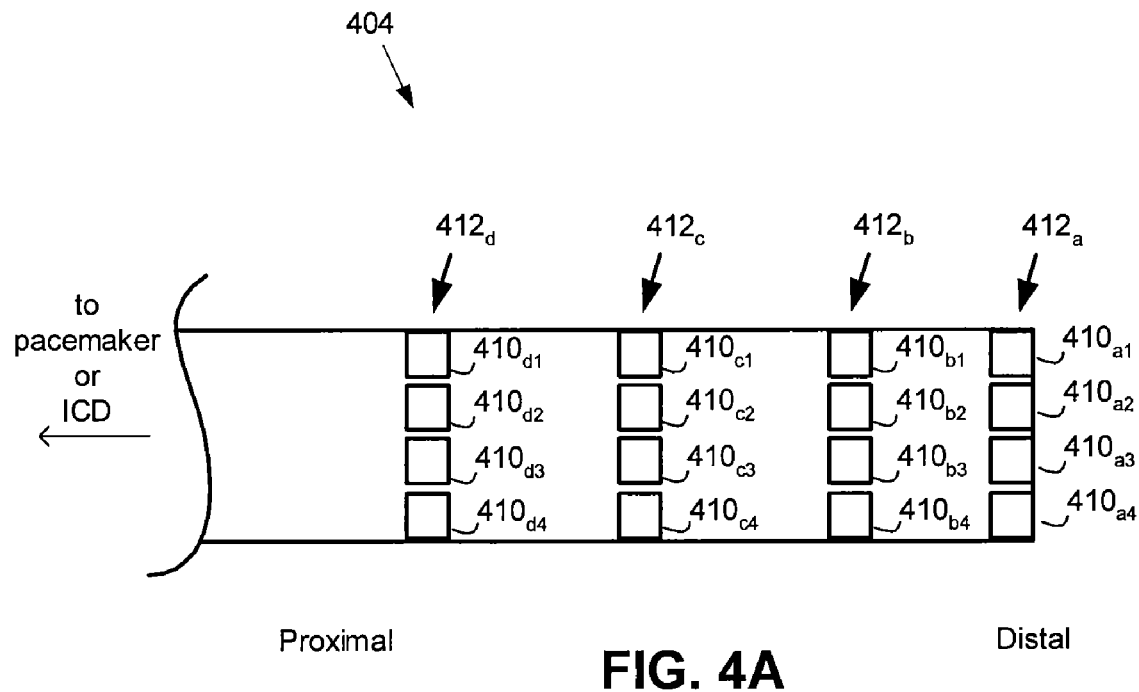
FIGS. 4A-4C schematically illustrate portions of exemplary multi-electrode leads with which embodiments of the present invention can be useful.

FIG. 4A illustrates a portion of an exemplary multi-electrode lead 404, which can be used with specific embodiments of the present invention. While not specifically shown in FIG. 4A, the lead 404 can be connected to the implantable cardiac stimulation device 110, e.g., in place of any of leads 120, 124 and/or 130. For the purpose of the following description, the lead 404 will be described as having a 4×4 matrix of electrodes, because the lead includes four arrays (also referred to as groups) of electrodes, each of which includes four electrodes 410. Each electrode 410 is electrically isolated from the other electrodes 410, but is capable of being electrically connected to other electrodes. Thus, exemplary lead 404 includes sixteen electrically isolated electrodes 410.

Figure 4B:
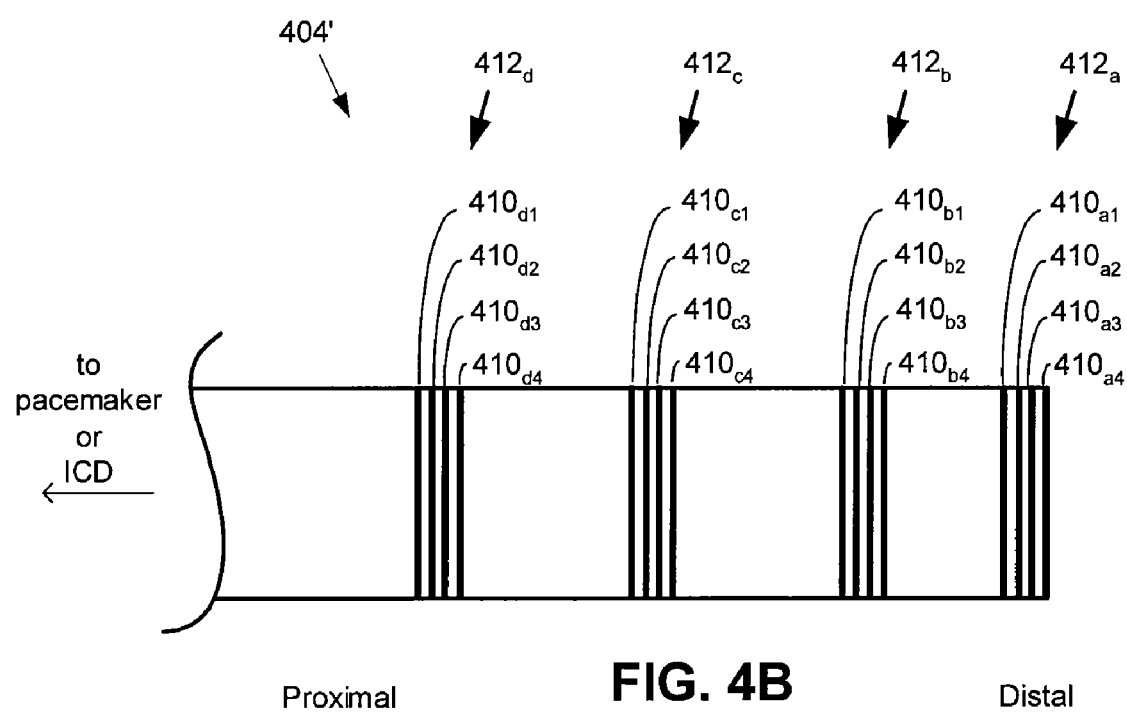
Figure 4C:
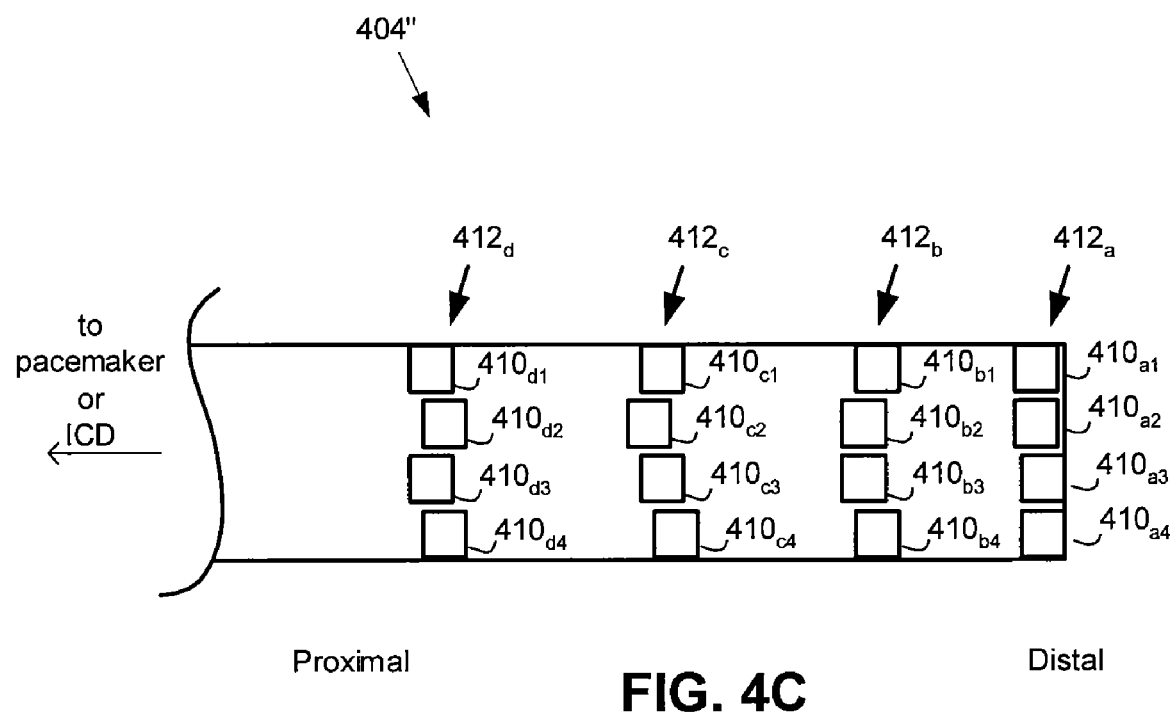

Each electrode of a same group of electrodes is generally located a similar distance distal from the implantable cardiac stimulation device 110 to which the lead 404 is connected. This is because electrodes of a same group are all within 5 mm of one another. As shown in FIG. 4A, a first group of electrodes $412_a$, which is most distal from the implantable cardiac stimulation device 110, includes electrodes $410_{a1}$, $410_{a2}$, $410_{a3}$ and $410_{a4}$. A second group of electrodes $412_b$, which is more proximal to the implantable cardiac stimulation device 110, includes electrodes $410_{b1}$, $410_{b2}$, $410_{b3}$ and $410_{b4}$. Also shown are a third group of electrodes $412_c$ and a fourth group of electrodes $412_d$. The groups of electrodes are shown schematically, and are not drawn to scale. For example, it may be that each electrode 410, of a group of electrodes 412, actually occupies slightly less than 90 degrees of a ring around a lead. Alternatively, electrodes 412 of a group 410 can be very closely spaced ring electrodes, e.g., as shown in FIG. 4B. FIG. 4C shows yet another example of groups 412 of electrodes 410. Other groups of electrodes are also possible, as one of ordinary skill in the art would appreciate from this description.

Electrodes of a same group are relatively close to one another, i.e., within 5 mm of one another. Electrodes of different groups are relatively further apart from one another, i.e., at least 10 mm apart.

Each electrode of a multi-electrode lead can have its own dedicated conductor through which signals can be transferred between the electrode and the implantable cardiac stimulation device (e.g., 110). For example, a multi-electrode lead disclosed in U.S. Pat. No. 6,978,178 (Sommer et al.), which is incorporated herein by reference, is shown as having seven electrodes and seven conductors. However, because of physical limitations, it is unlikely that a lead will have more than four conductors, but it is possible.

Alternatively, a multi-electrode lead can have circuitry within the lead that enables multiple electrodes to be selectively connected to a common conductor, thereby reducing the number of conductors within the lead to a more practical number. An example of such a multi-electrode lead is disclosed, for example, in U.S. Patent Publication No. 2006/0058588 (U.S. patent application Ser. No. 11/219,305), entitled "Methods and Apparatus for Tissue Activation and Monitoring" (Zdeblick), published Mar. 16, 2006 (filed Sep. 1, 2005), which is incorporated herein by reference above. Multi-electrode leads of the '588 patent publication include what are referred to as "satellites", where each satellite essentially includes a group of electrodes with switching and control circuitry that enables any electrode of a group to be connected to one of two conductors. Stated another way, each group of electrodes can be said to include switching and control circuitry. Such switching and control circuitry is controlled by a controller associated with a cardiac stimulation device (e.g., pacemaker), to which the lead is attached. Digital signals can be sent via the two conductors from the controller to the switching and control circuitry, to thereby control which electrode(s) is/are to be connected to which of the two conductors. Additionally, analog signals can be sent via the two conductors between the pacemaker and electrodes, for delivering pacing pulses, and sensing. The '588 patent publication discloses that one such lead can include, e.g., eight satellites, with each satellite including four electrodes, which would result in a lead having thirty-two electrodes. The electrodes of the leads 404, 404' and 404" of FIGS. 4A, 4B and 4C can be configured and controlled in a similar manner as those disclosed in the '588 patent publication. In other words, each group of electrodes of leads 404, 404' and 404" can include switching circuitry and control circuitry.

These are just a few examples of multi-electrode leads with which embodiments of the present invention can be used. However, embodiments of the present invention, unless stated otherwise, are not limited to use with the exemplary leads described herein.

Configuring a Multi-Electrode Lead

Pacing of the left side of the heart (i.e., left ventricle and/or left atrium) has been used, e.g., to improve cardiac function in heart failure patients. For a more specific example, left side pacing has been used for cardiac resynchronization therapy (CRT), which has been used to treat patients with congestive heart failure (CHF). A challenge with such left side pacing is that undesirable extracardiac stimulation often occurs, especially of the diaphragm and/or the phrenic nerve. Accordingly, it would be advantageous to reduce the probability of undesirable extracardiac stimulation caused when attempting to pace the left side of the heart.

Acute canine test results using a multi-electrode lead (similar to the one described with reference to FIG. 4A) have demonstrated the ability to eliminate extracardiac stimulation in an LV (cardiac vein) implant when the electrode used as the cathode and the electrode used as the anode are within 5 mm of one another (i.e., within a same group). This can be appreciated from a comparison between FIGS. 5A and 5B.

Figures 5A, 5B:
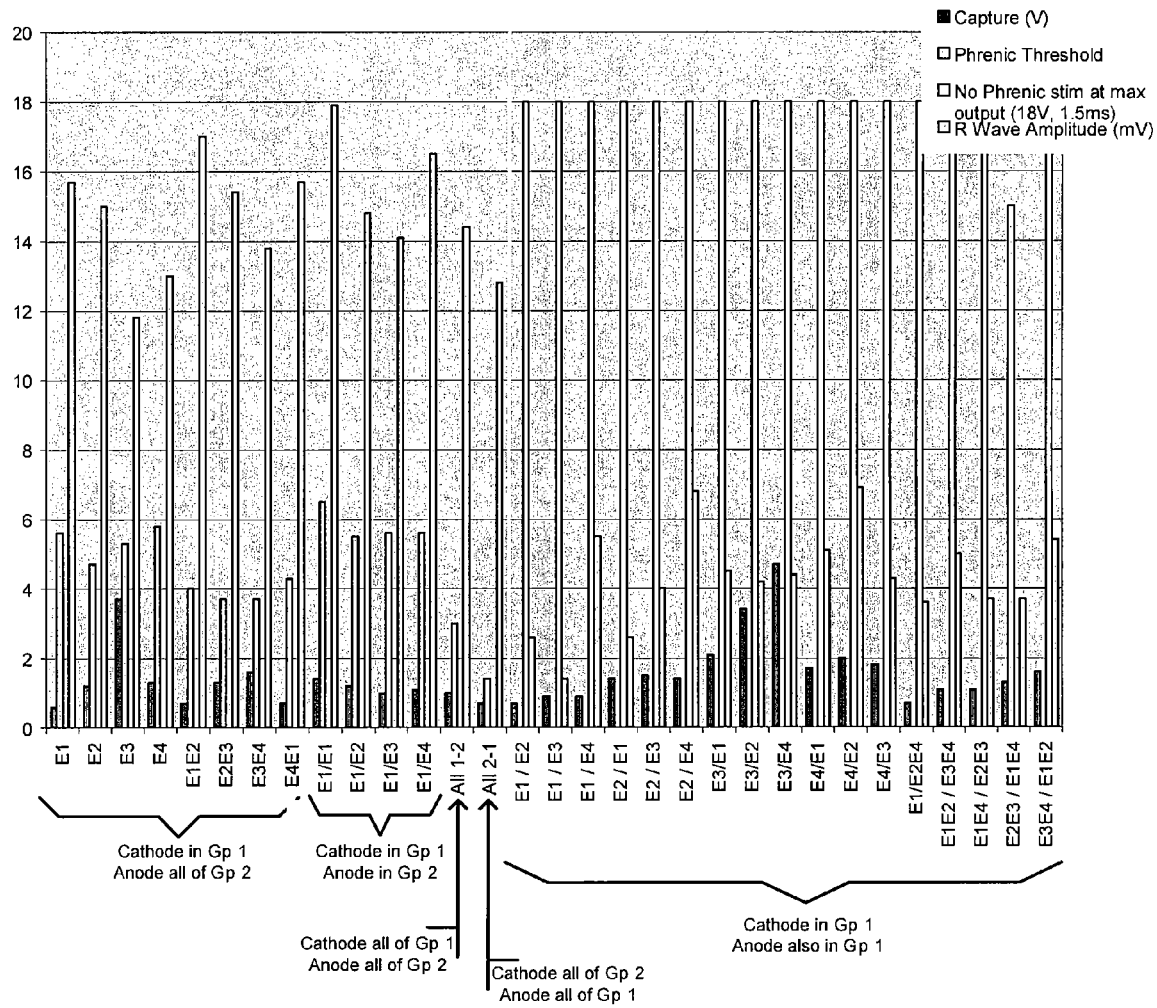
FIG. 5A is a graph that illustrates capture threshold levels, phrenic nerve stimulation threshold levels and sensed R wave amplitudes using various cathode-anode configurations of a multi-electrode lead (similar to the one of FIG. 4A), where the electrode(s) used as the cathode is/are at least 10 mm away from the electrode(s) uses as the anode.
FIG. 5B is a graph that illustrates capture threshold levels, phrenic nerve stimulation threshold levels and sensed R wave amplitudes using various cathode-anode configurations of a multi-electrode lead (similar to the one of FIG. 4A), where the electrode(s) used as the cathode and the electrode(s) used as the anode is/are within 5 mm of each other.

FIG. 5A illustrates capture threshold levels (left most bars of each group of three bars), phrenic nerve stimulation threshold levels (middle bars) and sensed R wave amplitudes (right most bars) using various configurations of a multi-electrode lead (similar to the one described in FIG. 4A). Here, the cathode is one or more electrode of a first group (e.g., 412a), and the anode is one or more electrode of a second group (e.g., 412b). For example, in FIG. 5A, the three bars above the label "E1" correspond to when the cathode is electrode 1 of the $1^{st}$ group (e.g., electrode $410_{a1}$ of group $412_a$), and the anode is all the electrodes of the $2^{nd}$ group (e.g., electrodes $410_{b1}$, $410_{b2}$, $410_{b3}$ and $410_{b4}$ of group $412_b$) electrically connected together; the three bars above the label "E1E2" correspond to when the cathode is the $1^{st}$ and $2^{nd}$ electrodes of the $1^{st}$ group (e.g., electrodes $410_{a1}$ and $410_{a2}$ of group $412_a$) electrically connected together, and the anode is all the electrodes of the $2^{nd}$ group (e.g., electrodes $410_{b1}$, $410_{b2}$, $410_{b3}$ and $410_{b4}$ of group $412_b$) electrically connected together; and the three bars above the label "E1/E2" correspond to when the cathode is the $1^{st}$ electrode of the $1^{st}$ group (e.g., electrode $410_{a1}$ of group $412_a$), and the anode is the $2^{nd}$ electrode the $2^{nd}$ group (e.g., electrode $410_{b2}$ of group $412_b$).

In FIG. 5A, capture thresholds ranged from about 0.5V to about 3.5V, sensed R wave amplitudes ranged from about 10.5V to 18V, and phrenic nerve stimulation thresholds ranged from about 1.5V to 6.5V. As will be described in more detail below, it is desired that the capture threshold not exceed a maximum acceptable capture threshold, and that the sensed intrinsic R-wave amplitude reach at least a minimum acceptable sensing threshold. The maximum acceptable capture threshold and the minimum acceptable sensing threshold can be entered, e.g., by a clinician or other user, into an external programmer (e.g., 202). It is also desired that phrenic nerve stimulation be avoided. To avoid phrenic nerve stimulation, the phrenic nerve stimulation threshold for an electrode configuration should be greater (and preferably, at least a specific margin greater) than the capture threshold for that electrode configuration. In summary, FIG. 5A illustrates that acceptable capture threshold levels and sensed R-wave amplitudes can be achieved by having the anode and the cathode be electrodes of separate groups (i.e., electrodes separated from one another by at least 10 mm), but that such electrode configurations may result in phrenic nerve stimulation threshold levels that are lower than desired.

FIG. 5B illustrates capture threshold levels (left most bars), phrenic nerve stimulation threshold levels (middle bars) and sensed R wave amplitudes (right most bars) using various configurations of a multi-electrode lead (similar to the one described in FIG. 4A). Here, the cathode is one or more electrode in a first group (e.g., 412a), and the anode is one or more electrodes of the same group (e.g., 412a). In other words, the electrode(s) used as the cathode is within 5 mm of the electrode(s) used as the anode. For example, in FIG. 5B, the three bars above the label "E1/E2" correspond to when the cathode is electrode 1 of the $1^{st}$ group (e.g., electrode $410_{a1}$ of group $412_a$), and the anode is electrode 2 of the $1^{st}$ group (e.g., electrode $410_{a2}$ of group $412_a$); and the three bars above the label "E1E2/E3E4" correspond to when the cathode is the $1^{st}$ and $2^{nd}$ electrodes of the $1^{st}$ group (e.g., electrodes $410_{a1}$ and $410_{a2}$ of group $412_a$) electrically connected together, and the anode is the $3^{rd}$ and $4^{th}$ electrodes of the 1st group (e.g., electrodes $410_{a3}$ and $410_{a4}$ of group $412_a$) electrically connected together.

In FIG. 5B, capture voltages ranged from about 0.5V to about 4.5V, and sensed R wave amplitudes ranged from only about 1.5V to 4V. Impressively, no phrenic nerve stimulation occurred even where pacing pulses of 18V, 1.5 ms were delivered. In summary, FIG. 5B illustrates that acceptable capture threshold levels, and avoidance of phrenic nerve stimulation can be achieved by having the anode and the cathode be electrodes of the same group (i.e., within 5 mm of one another), but that some such electrode configurations result in sensed R-wave amplitudes that may be lower than desired.

FIGS. 4A, 4B and 4C discussed above illustrate exemplary leads 404, 404' and 404" that each have four groups of electrodes, with each group of electrodes including four electrodes, resulting in each lead having a total of sixteen electrodes. Such leads can be used to implement embodiments of the present invention. When using a lead such as those in FIGS. 4A, 4B and 4C, the cathode can be one or more electrode in a group, and the anode can be one or more electrode of that same group (which may, or may not be electrically connected with one or more electrode of another group).

However, embodiments of the present invention are not limited to use with multi-electrode leads that are similar to those described with reference to FIGS. 4A, 4B and 4C. Rather, certain embodiments of the present invention can be used with any lead that includes multiple groups of electrodes. Benefits of using what is referred to as a "distributed" anode configuration, where one electrode of the anode is within 5 mm of the cathode (i.e., in the same group as the cathode electrode), but another electrode of the anode is at least 10 mm from the cathode (i.e., in a different group than the cathode electrode), are discussed in commonly invented and commonly assigned U.S. patent application Ser. No. 11/688,941, entitled "Distributed Anode Cardiac Pacing and Sensing", filed Mar. 21, 2007 (Shelchuk), which is incorporated herein by reference. Embodiments of the present invention contemplate the use of a distributed anode.

Set-Up Algorithms

Figure 6:
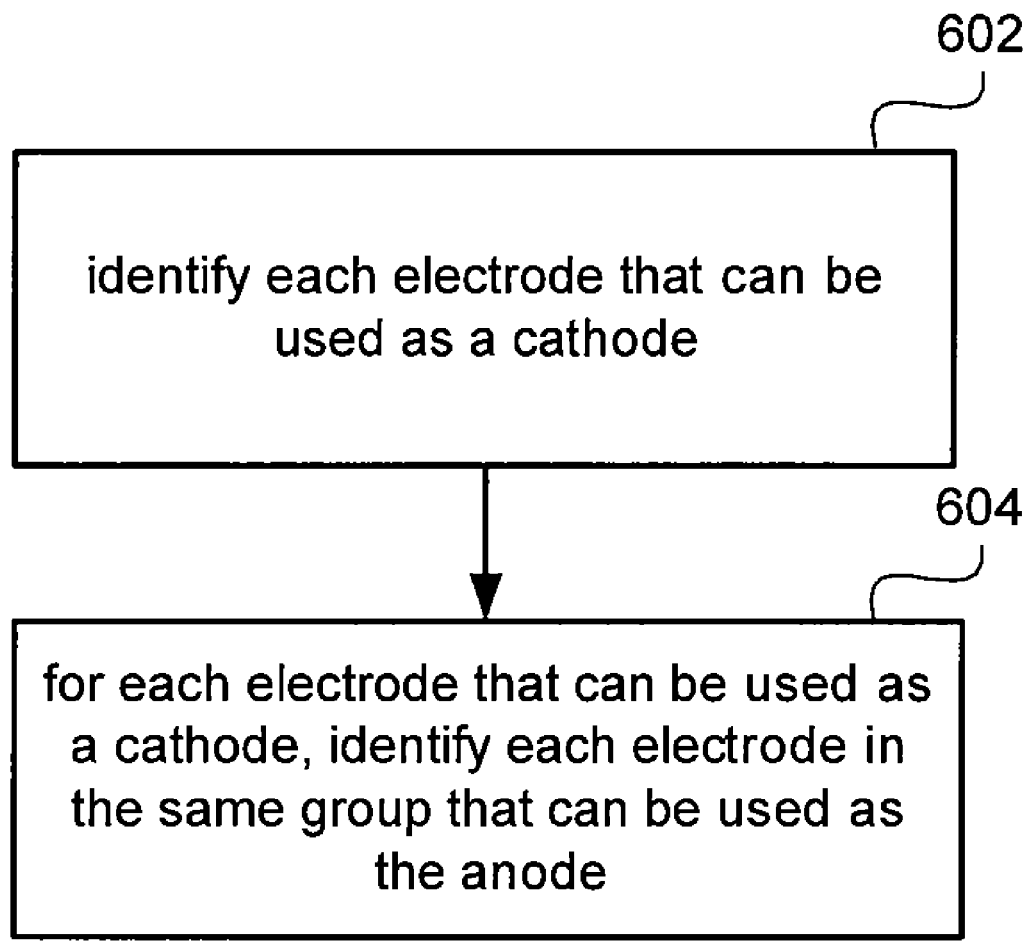
FIG. 6 is a high level flow diagram that is used to explain how acceptable cathode-anode electrode configurations can be identified, in accordance with specific embodiments of the present invention.
Figure 7:
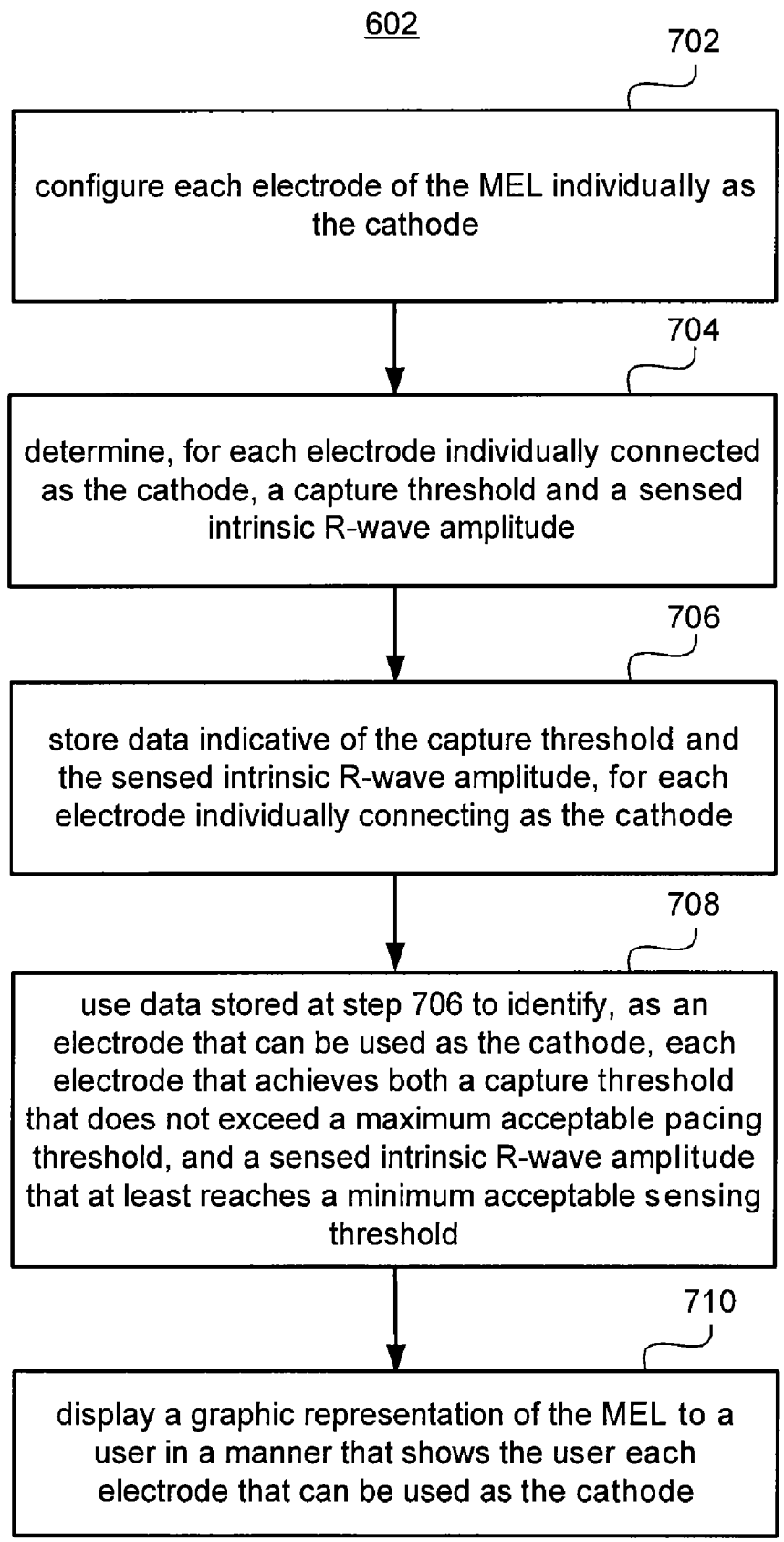
FIG. 7 is a high level flow diagram that provides additional details of the step of FIG. 6 where electrodes that can be used as a cathode are identified, in accordance with specific embodiments of the present invention.
Figure 8:
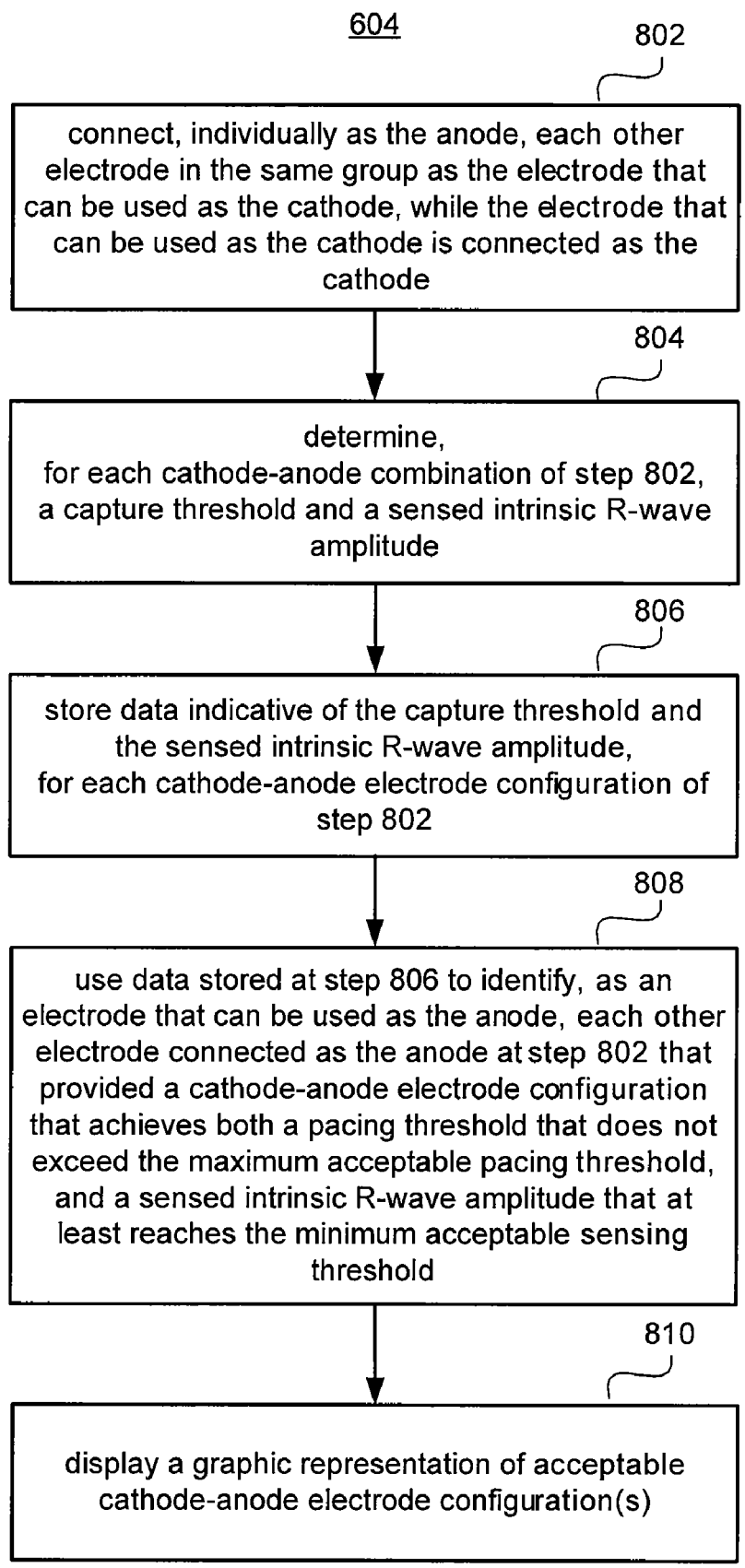
FIG. 8 is a high level flow diagram that provides additional details of the step of FIG. 6 where electrodes that can be used as an anode are identified, in accordance with specific embodiments of the present invention.

Certain embodiments of the present invention shall now be summarized with reference to the high level flow diagrams of FIGS. 6-8. More specifically, embodiments of the present invention described with reference to FIGS. 6-8 can be used to identify in an efficient manner cathode-anode electrode configurations that can be used to not exceed a maximum acceptable capture threshold, and that provide a sensed intrinsic R-wave amplitude of at least a minimum acceptable sensing threshold. The maximum acceptable capture threshold and the minimum acceptable sensing threshold can be entered, e.g., by a clinician, into an external programmer (e.g., 202) that controls performance of the set-up algorithm. One or both of these thresholds can be defaults (or so-called nominals), if not entered by a user.

Such embodiments are for use with an implantable system that includes an implantable cardiac stimulation device (e.g., 110) to which is attached a multi-electrode lead (MEL) (e.g., 404) that includes N groups of electrodes, with each of the N groups including at least M electrodes, where N≧2 and M is ≧2. As mentioned above, electrodes in a same group are within 5 mm of one another, and electrodes in separate groups are at least 10 mm from one another. Examples of such multi-electrode leads were described above in the discussion of FIGS. 4A-4C. However, embodiments of the present invention are not limited to use with those exemplary leads.

Referring to FIG. 6, at a step 602, each electrode that can be used as a cathode is identified. Then, at a step 604, for each for each electrode that can be used as the cathode, one or more other electrode in the same group that can be used as a corresponding anode is identified. The motivation for having the cathode and anode be electrodes of the same group are the results of the acute canine tests discussed above, with reference to FIGS. 5A and 5B. Those studies have demonstrated how such configurations can be used to eliminate extracardiac stimulation in an LV (cardiac vein) implant. Additional details of step 602 are described below with reference to the high level flow diagram of FIG. 7. Additional details of step 604 are described below with reference to the high level flow diagram of FIG. 8. The steps of FIGS. 6, 7 and 8 can be performed under the control of a non-implantable device (e.g., external programmer 202) in communication with the implantable cardiac stimulation device (e.g., 110).

Referring to FIG. 7, at a step 702, each electrode of the multi-electrode lead (MEL) is connected individually as the cathode. Referring back to FIGS. 1B and 4A-4C, step 704 can be accomplished, e.g., through appropriate control of the switch bank 274 (of FIG. 1B). Additionally, where each group of electrodes of the an MEL includes switching circuitry, step 704 may also require appropriate control of the switching circuitry within the MEL lead, e.g., lead 404, 404' or 404" of FIGS. 4A-4C.

At step 702, when an electrode is individually connected as the cathode (for the purpose of testing the electrode's candidacy as a cathode), one or more electrode on the same MEL or on a different lead is connected as the anode, or an electrically conductive housing (e.g., 240) of the implantable cardiac stimulation device is connected as the anode. In accordance with specific embodiments, when an electrode is individually connected as the cathode at step 702 (for the purpose of testing the electrode's candidacy as a cathode), all the electrodes in another group of electrodes are electrically connected together as the anode. For example, all the electrodes in an adjacent group of electrodes can be electrically connected together as the anode. In a specific embodiment, when an electrode has two adjacent groups of electrodes, the more proximal group of electrodes is electrically connected together as the anode. In accordance with alternative embodiments, when an electrode is individually connected as the cathode at step 702 (for the purpose of testing the electrode's candidacy as a cathode), all the other electrodes in the same group of electrodes are electrically connected together as the anode.

At a step 704, for each electrode that is individually connected as the cathode, a capture threshold and a sensed intrinsic R-wave amplitude are determined. The capture threshold, as mentioned above, is defined as the lowest stimulation pulse energy at which capture (i.e., successful depolarization and contraction of a cardiac chamber) occurs. The capture threshold can be determined, e.g., by using an autocapture algorithm, or other known capture threshold determining algorithm, which is also known as capture threshold detection algorithm. The sensed intrinsic R-wave amplitude is simply the R-wave amplitude that is sensed using an electrode configuration, which is easily measured from an EGM.

In an exemplary capture threshold detection algorithm, the stimulation energy is initially set to a high or maximum value. The stimulation energy is then progressively decreased in increments by decrementing either the pulse width and/or the pulse amplitude until loss of capture is detected. Capture verification during the threshold test can be performed by setting a capture detection window following the stimulation pulse and searching for an evoked response within that window. The evoked response may be detected by a signal that exceeds a predefined sensing threshold, by comparing the sampled signal to a template model of an evoked response, or by detecting T-waves, mechanical heart contraction, changes in cardiac blood volume impedance, or another signature of a contracting chamber, or by other means known in the art. If there is loss of capture associated with two consecutive beats at a stimulation energy level, this can be interpreted as being a subthreshold. At that time, the stimulation energy can be progressively increased in smaller increments until capture is confirmed on two consecutive pulses. The pulse energy level at this point can be considered that capture threshold. This is but one example of a capture threshold detection algorithms. As is known in the art, there are many alternatives to this exemplary algorithm. In a specific embodiment, a lowest output setting that results in capture on consecutive pulses starting from a lower value where there is loss of capture can be considered the capture threshold. Details of exemplary autocapture algorithms are provided in U.S. Pat. No. 5,350,410, entitled "Autocapture System for Implantable Pulse Generator" (Kleks et al.) and U.S. Pat. No. 7,031,773, entitled "Implantable Cardiac Stimulation System Providing Autocapture and Lead Impedance Assessment and Method" (Levine et al.), both of which are incorporated herein by reference.

Still referring to FIG. 7, at a step 706, data indicative of the capture threshold and the sensed intrinsic R-wave amplitude are stored for each electrode individually connecting as the cathode. Such data can be stored, e.g., in the memory (e.g., 294) of the implantable stimulation device and/or in the memory of the external programmer or other external device. Steps 702-706 are sometimes referred to hereafter as the "scan process".

At a step 708, the data stored at step 706 is used to identify each electrode that achieves both a capture threshold that does not exceed a maximum acceptable capture threshold, and a sensed intrinsic R-wave amplitude that at least reaches a minimum acceptable sensing threshold, as an electrode that can be used as the cathode.

Additionally, at a step 710, a graphical representation of the MEL can be displayed to a user in a manner that shows the user each electrode that can be used as the cathode. This will be described in more detail below with reference to FIGS. 9A-9C. Such information can also be provided to a user in a textual manner, or a combination of a graphical and textual manner.

FIG. 8 will now be used to summarize how candidate anode(s) can be identified, once candidate cathode(s) have been identified using steps 702-708. Referring to FIG. 8, at a step 802, each other electrode (in the same group as an electrode that can be used as the cathode) is individually connected as the anode, while the electrode that can be used as the cathode is connected as the cathode. Referring back to FIGS. 1B and 4A-4C, step 802 can be accomplished, e.g., through appropriate control of the switchbank 274 (of FIG. 1B) and the switching circuitry within the MEL leads 404, 404' or 404" (of FIGS. 4A-4C).

At a step 804, for each cathode-anode combination of step 802, a capture threshold and a sensed intrinsic R-wave amplitude are determined.

At a step 806, data indicative of the capture threshold and the sensed intrinsic R-wave amplitude is stored, for each cathode-anode electrode configuration of step 802.

At a step 808, the data stored at step 806 is used to identify, as an electrode that can be used as the anode, each other electrode connected as the anode at step 802 that provided a cathode-anode electrode configuration that achieves both a capture threshold that does not exceed the maximum acceptable capture threshold, and a sensed intrinsic R-wave amplitude that at least reaches the minimum acceptable sensing threshold. It is presumed that phrenic nerve stimulation will be avoided, because phrenic nerve stimulation threshold levels are extremely high when an electrode connected as the cathode and an electrode connected as the anode are electrodes of a same group (i.e., electrodes within 5 mm of one another), as was explained above with reference to FIG. 5B.

Additionally, at a step 810, a graphical representation of the MEL can be displayed to a user in a manner that shows the user acceptable cathode-anode combinations. Such information can also be provided textual, or as a combination of text and graphics. This will be described in more detail below with reference to FIGS. 9A-9C.

In accordance with specific embodiments of the present invention, after candidate cathode(s) is/are initially identified (i.e., after step 602 is initially performed), a user can adjust at least one of the maximum acceptable capture threshold, and the minimum acceptable sensing threshold, e.g., using an external programmer (e.g., 202) or other external device. Thereafter, alternative and/or additional candidate cathode(s) can be identified based on the data already stored, and the adjusted user specified thresholds. More specifically, referring back to FIG. 7, steps 708 and 710 can be repeated in view of the adjustment, using the data stored at step 706, without repeating steps 702, 704 and 706. For example, this can allow the screen displayed at step 710 to be updated substantially instantaneously, because a new "scan process" would not be required.

In specific embodiments, where a group of electrodes includes three or more electrodes, step 802 can also include connecting together, as the anode, combinations of other electrodes in the same group as the electrode that can be used as the cathode, while the electrode that can be used as the cathode is connected as the cathode. In such embodiments, step 808 (and 810) can also include identifying (and displaying) multiple electrode combinations that can be used as the anode. Distributed anode configurations can also be tested, if desired.

Figure 9A:
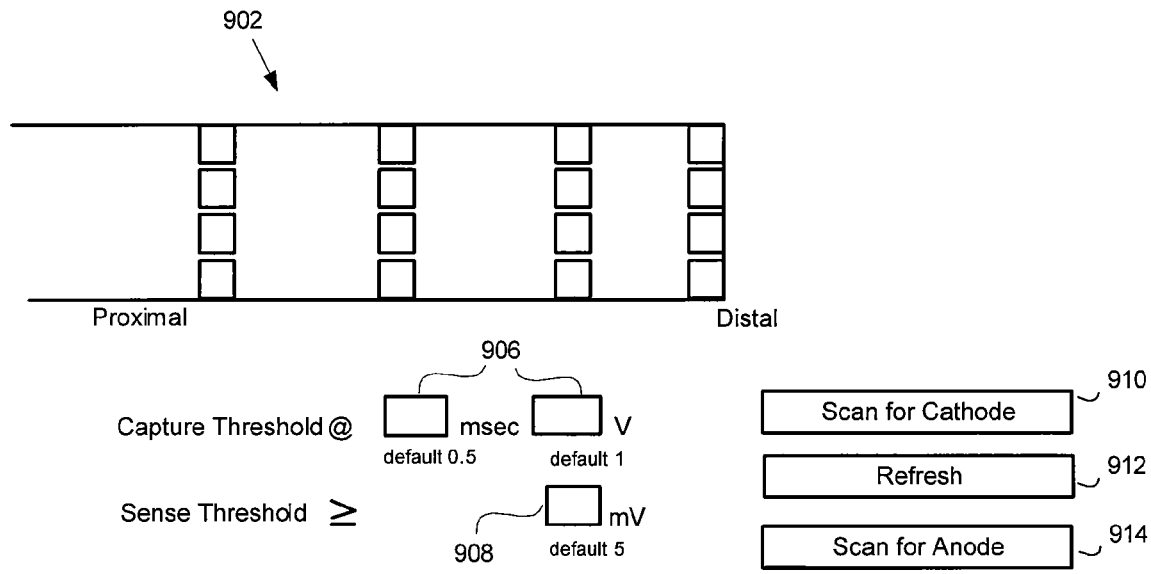
FIG. 9A illustrates an exemplary initial graphical representation of a multi-electrode lead that can be displayed to a user.
Figure 9B:
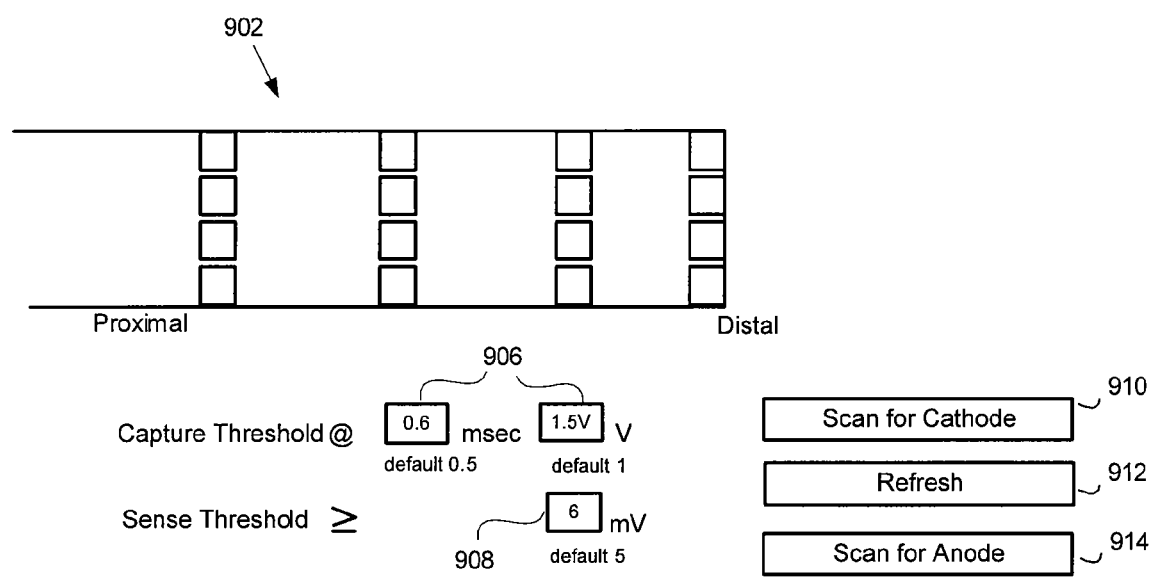
FIG. 9B illustrates an exemplary graphical representation that can be presented to a user after one or more electrode that is a candidate as the cathode is identified.
Figure 9C:
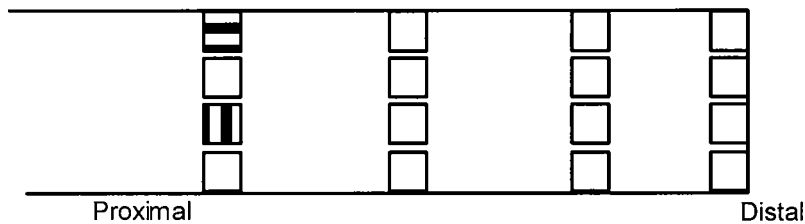
FIG. 9C illustrates an exemplary graphical representation of multiple candidate cathode-anode electrode configurations that can be presented to a user.
Figure 9C:
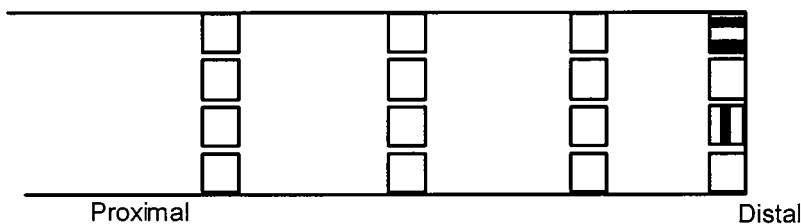

FIGS. 9A-9C will now be used to show an exemplary graphical user interface (GUI), which can be displayed, e.g., on a display of an external programmer (e.g., 202) or other external system. Referring to FIG. 9A, initially a graphical representation 902 of a MEL is displayed. Additionally, fields 906 for entering the maximum acceptable capture threshold, and a field 908 for entering the minimum acceptable sensing threshold are displayed. Further, graphical buttons, including a "scan for cathode" button 910, a "refresh" button 912 and a "scan for anode" button 914 are shown.

Initially the fields 906 and 908 can be empty, with predetermined defaults (e.g., shown under the fields) being used if the user does not enter values into the fields. Alternatively, the defaults can initially occupy the fields. Also, initially all the buttons except the "scan for cathode" button 910 may be grayed out (or alternatively, the "scan for cathode" button 910 can be highlighted) in a manner that specifies to the user which action(s) is/are appropriate at the time.

Presume that the user enters 0.6 msec and 1.5 V into fields 906 and 6 mV into field 908, and then presses the "scan for cathode" button 910. This will result in steps 702-710 being performed. A resulting display is shown in FIG. 9B. At step 710, in this example, the electrodes that are not candidates for use as the cathode are grayed out. Alternative, or additionally, the electrodes that are candidates for use as the cathode can be highlighted. Additionally, the "scan for cathode" button 910 can now be grayed out, while the "refresh" button 912 and "scan for anode" button 914 are not grayed out. At this point the user can change the maximum acceptable capture threshold and/or the minimum acceptable sensing threshold, and press the "refresh" button 912. Alternatively, the user can press the "scan for anode" button 914.

If the user changes the maximum acceptable capture threshold and/or the minimum acceptable sensing threshold and then presses the "refresh" button 912, steps 708 and 710 can be repeated in view of the adjustment, using the data stored at step 706, without repeating steps 702, 704 and 706. This allows the candidate cathodes to updated substantially instantaneously, because a new "scan process" would not be required, as mentioned above.

After the user presses the "scan for anode" button, then steps 802-810 will be performed. At step 810, the candidate cathode-anode electrode configurations are displayed to the user. The candidate cathode-anode electrode configurations can be shown to the user in a series of figures. Such series of figures can be displayed to the user at once, as shown in FIG. 9C. Alternatively, one candidate configuration can be displayed to the user at a time, and the user can tab, scroll or otherwise move through the possibilities. Where multiple options are presented to a user, the user can select a best option based on which configuration provides a lowest capture threshold, or based on some other criteria. Thereafter the user can configure the implantable stimulation device and MEL to use the selected cathode-anode electrode configuration for pacing and sensing. In specific embodiments, the user can simply select, via the external programmer or other external device, one of the options displayed to the user, and the external programmer or other external device can thereafter appropriately configure the implantable stimulation device and MEL (e.g., using telemetry) without requiring further input by the user.

In an alternative embodiment, only the best candidate as the cathode is presented to the user at step 710, where the "best" cathode is the electrode that has the lowest capture threshold of all electrodes that meet the user-selected (or default) criteria. Additionally, the set-up time can be reduced by only performing steps 802-808 for the best cathode. Thereafter, only the best cathode-anode electrode configuration can be displayed to the user at step 810, where the best cathode-anode electrode configuration has the lowest capture threshold of all the identified cathode-anode electrode configurations that meet the user-selected (or default) criteria.

Specific embodiments of the present invention are useful from expediting set up of a multi-electrode lead (MEL). While MELs are especially useful for pacing and sensing in the left ventricle of a patient's heart, such leads can be used for pacing and sensing in other cardiac chambers.

Embodiments of the present invention can be used for the initial set-up of a MEL, i.e., at the time of implantation of the MEL. Additionally, or alternatively, embodiments of the present invention can be used to reconfigure an MEL during a patient's follow up visit to a medical facility. Such reconfigurations can useful where lead placement may have moved, where there is fibrotic encapsulation of electrodes after implantation, etc. Is it also possible that such reconfiguration can be performed autonomously by the implanted device, without any assistance of an external device.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with an implantable system that includes
an implantable cardiac stimulation device and a multi-electrode lead (MEL) that includes N groups of electrodes,
with each of the N groups including at least M electrodes, where N≧2 and M is ≧2,
where electrodes in a same group are within 5 mm of one another, and
where electrodes in separate groups are at least 10 mm from one another,
a method for identifying cathode-anode electrode configurations that can be used to not exceed a maximum acceptable capture threshold, and that provide a sensed intrinsic R-wave amplitude of at least a minimum acceptable sensing threshold,
the method comprising:
(a) identifying each electrode that can be used as a cathode by
(a.1) connecting each electrode of the MEL individually as the cathode;
(a.2) determining, for each electrode individually connected as the cathode, a capture threshold and a sensed intrinsic R-wave amplitude;
(a.3) storing data indicative of the capture threshold and the sensed intrinsic R-wave amplitude, for each electrode individually connecting as the cathode; and
(a.4) identifying, as an electrode that can be used as the cathode, each electrode that achieves both a capture threshold that does not exceed a maximum acceptable capture threshold, and a sensed intrinsic R-wave amplitude that at least reaches a minimum acceptable sensing threshold, said identifying based on the data stored at (a.3);
(b) for each electrode of the MEL identified as an electrode that can be used as the cathode, identifying one or more other electrode in the same group that can be used as a corresponding anode by
(b.1) connecting, individually as the anode, each other electrode in the same group as the electrode that can be used as the cathode, while the electrode that can be used as the cathode is connected as the cathode;
(b.2) determining, for each cathode-anode combination of (b.1), a capture threshold and a sensed intrinsic R-wave amplitude;
(b.3) storing data indicative of the capture threshold and the sensed intrinsic R-wave amplitude, for each cathode-anode electrode configuration of (b.1); and
(b.4) identifying, as an electrode that can be used as the anode, each other electrode connected as the anode at (b.1) that provided a cathode-anode electrode configuration that achieves both a capture threshold that does not exceed the maximum acceptable capture threshold, and a sensed intrinsic R-wave amplitude that at least reaches the minimum acceptable sensing threshold, said identifying based on the data stored at (b.3).

2. The method of claim 1, wherein at step (a), when a said electrode is individually connected as the cathode, all the electrodes in another group of electrodes electrically are connected together as the anode.

3. The method of claim 1, wherein at step (a), when a said electrode is individually connected as the cathode, all the electrodes in an adjacent group of electrodes are electrically connected together as the anode.

4. The method of claim 3, wherein at step (a), when an electrode has two adjacent groups of electrodes, the more proximal group of electrodes are electrically connected together as the anode.

5. The method of claim 1, wherein at step (a), when a said electrode is individually connected as the cathode, all the other electrodes in the same group of electrodes are electrically connected together as the anode.

6. The method of claim 1, wherein at step (a), when a said electrode is individually connected as the cathode, one or more electrode on the same MEL or on a different lead is connected as the anode, or an electrically conductive housing of the implantable cardiac stimulation device is connected as the anode.

7. The method of claim 1, wherein steps (a) and (b) are performed under the control of a non-implantable device in communication with the implantable cardiac stimulation device.

8. The method of claim 1, further comprising:
after step (a) is performed, allowing a user to adjust at least one of the maximum acceptable capture threshold, and the minimum acceptable sensing threshold; and
repeating (a.4) in view of the adjustment, using the data stored at (a.3), without repeating (a.1), (a.2) and (a.3).

9. The method of claim 1, wherein where a group includes 3 or more electrodes:
(b.1) also includes connecting together, as the anode, combinations of other electrodes in the same group as the electrode that can be used as the cathode, while the electrode that can be used as the cathode is connected as the cathode; and
(b.4) also includes identifying multiple electrode combinations that can be used as the anode.

10. The method of claim 1, wherein:
step (a) further comprises (a.5) displaying a graphical representation of the MEL to a user in a manner that shows the user each electrode that can be used as the cathode; and
step (b) further comprises (b.5) displaying a graphical representation of each cathode-anode electrode configuration that achieves both a capture threshold that does not exceed the maximum acceptable capture threshold, and a sensed intrinsic R-wave amplitude that at least reaches the minimum acceptable sensing threshold.

11. For use with an implantable system that includes
an implantable cardiac stimulation device and a multi-electrode lead (MEL) that includes N groups of electrodes,
with each of the N groups including at least M electrodes, where N≧2 and M is ≧2,
where electrodes in a same group are within 5 mm of one another, and
where electrodes in separate groups are at least 10 mm from one another,
a method for identifying a preferred cathode-anode electrode configuration that can be used to not exceed a maximum acceptable capture threshold, and that provide a sensed intrinsic R-wave amplitude of at least a minimum acceptable sensing threshold,
the method comprising:
(a) identifying a preferred electrode for use as a cathode by
(a.1) configuring each electrode of the MEL individually as the cathode;
(a.2) determining, for each electrode individually connected as the cathode, a capture threshold and a sensed intrinsic R-wave amplitude;
(a.3) storing data indicative of the capture threshold and the sensed intrinsic R-wave amplitude, for each electrode individually connecting as the cathode; and
(a.4) identifying, as the preferred electrode for use as the cathode, the electrode that achieves both a lowest capture threshold not exceeding the maximum acceptable capture threshold, and a sensed intrinsic R-wave amplitude that at least reaches a minimum acceptable sensing threshold, said identifying based on the data stored at (a.3);
(b) identifying a preferred electrode for use as an anode by
(b.1) connecting, individually as the anode, each other electrode in the same group as the preferred electrode for use as the cathode, while the preferred electrode for use as the cathode is connected as the cathode;
(b.2) determining, for each cathode-anode combination of (b.1), a capture threshold and a sensed intrinsic R-wave amplitude;
(b.3) storing data indicative of the capture threshold and the sensed intrinsic R-wave amplitude, for each cathode-anode electrode configuration of (b.1); and
(b.4) identifying, as the preferred electrode for use as the anode, the electrode connected as the anode at (b.1) that provided the cathode-anode electrode configuration that achieves both a lowest capture threshold, and a sensed intrinsic R-wave amplitude that at least reaches the minimum acceptable sensing threshold, said identifying based on the data stored at (b.3).

12. The method of claim 11, wherein at step (a), when a said electrode is individually connected as the cathode, all the electrodes in another group of electrodes electrically connected together as the anode.

13. The method of claim 11, wherein at step (a), when a said electrode is individually connected as the cathode, all the electrodes in an adjacent group of electrodes are electrically connected together as the anode.

14. The method of claim 13, wherein at step (a), when an electrode has two adjacent groups of electrodes, the more proximal group of electrodes are electrically connected together as the anode.

15. The method of claim 11, wherein at step (a), when a said electrode is individually connected as the cathode, all the other electrodes in the same group of electrodes are electrically connected together as the anode.

16. The method of claim 11, wherein at step (a), when a said electrode is individually connected as the cathode, one or more electrode on the same MEL or on a different lead is connected as the anode, or an electrically conductive housing of the implantable cardiac stimulation device is connected as the anode.

17. The method of claim 11, wherein steps (a) and (b) are performed under the control of a non-implantable device in communication with the implantable cardiac stimulation device.

18. The method of claim 11, further comprising:
after step (a) is performed, allowing a user to adjust at least one of the maximum acceptable capture threshold, and the minimum acceptable sensing threshold; and
repeating (a.4) in view of the adjustment, using the data stored at (a.3), without repeating (a.1), (a.2) and (a.3).

19. The method of claim 11, wherein where a group includes 3 or more electrodes:
(b.1) also includes connecting together, as the anode, combinations of other electrodes in the same group as the preferred electrode for use as the cathode, while the preferred electrode for use as the cathode is connected as the cathode; and
(b.4) also includes identifying multiple electrode combinations that can be used as the anode.

20. The method of claim 11, wherein:
step (a) further comprises (a.5) displaying a graphical representation of the MEL to a user in a manner that shows the user the preferred electrode for use as the cathode; and step (b) further comprises (b.5) displaying a graphical representation of a preferred cathode-anode electrode configuration.

21. For use with an implantable system that includes
an implantable cardiac stimulation device and a multi-electrode lead (MEL) that includes N groups of electrodes,
with each of the N groups including at least M electrodes, where $N \geq 2$ and M is $\geq 2$,
where electrodes in a same group are within 5 mm of one another, and
where electrodes in separate groups are at least 10 mm from one another,
a method for identifying cathode-anode electrode configurations that can be used to not exceed a maximum acceptable capture threshold, and that provide a sensed intrinsic R-wave amplitude of at least a minimum acceptable sensing threshold,
the method comprising:
(a) identifying, as an electrode that can be used as the cathode, each electrode that achieves both a capture threshold that does not exceed a maximum acceptable capture threshold, and a sensed intrinsic R-wave amplitude that at least reaches a minimum acceptable sensing threshold, and storing data indicative thereof; and
(b) for each electrode of the MEL identified as an electrode that can be used as the cathode, identifying as an electrode that can be used as a corresponding anode, each other electrode in the same group as the electrode that can be used as the cathode, that provides a cathode-anode electrode configuration that achieves both a capture threshold that does not exceed the maximum acceptable capture threshold, and a sensed intrinsic R-wave amplitude that at least reaches the minimum acceptable sensing threshold, and storing data indicative thereof.

22. For use with an implantable system that includes
an implantable cardiac stimulation device and a multi-electrode lead (MEL) that includes N groups of electrodes,
with each of the N groups including at least M electrodes, where $N \geq 2$ and M is $\geq 2$,
where electrodes in a same group are within 5 mm of one another, and
where electrodes in separate groups are at least 10 mm from one another,
a method for identifying cathode-anode electrode configurations that can be used to not exceed a maximum acceptable capture threshold,
the method comprising:
(a) identifying each electrode that can be used as a cathode by
  (a.1) connecting each electrode of the MEL individually as the cathode;
  (a.2) determining, for each electrode individually connected as the cathode, a capture threshold;
  (a.3) storing data indicative of the capture threshold, for each electrode individually connecting as the cathode; and
  (a.4) identifying, as an electrode that can be used as the cathode, each electrode that achieves a capture threshold that does not exceed a maximum acceptable capture threshold, said identifying based on the data stored at (a.3);
(b) for each electrode of the MEL identified as an electrode that can be used as the cathode, identifying one or more other electrode in the same group that can be used as a corresponding anode by
  (b.1) connecting, individually as the anode, each other electrode in the same group as the electrode that can be used as the cathode, while the electrode that can be used as the cathode is connected as the cathode;
  (b.2) determining, for each cathode-anode combination of (b.1), a capture threshold;
  (b.3) storing data indicative of the capture threshold, for each cathode-anode electrode configuration of (b.1); and
  (b.4) identifying, as an electrode that can be used as the anode, one or more other electrode connected as the anode at (b.1) that provided a cathode-anode electrode configuration that achieves a capture threshold that does not exceed the maximum acceptable capture threshold, said identifying based on the data stored at (b.3).

* * * * *